United States Patent [19]

Leach

[11] 4,084,006

[45] Apr. 11, 1978

[54] METHOD OF USING DIALKYLPHENOLS AN ANTIVIRAL AGENTS

[76] Inventor: Byron E. Leach, 1550 N. Parkway, No. 115, Memphis, Tenn. 38112

[21] Appl. No.: 779,951

[22] Filed: Mar. 21, 1977

Related U.S. Application Data

[63] Continuation-in-part of Ser. No. 697,530, Jun. 18, 1976, abandoned, which is a continuation of Ser. No. 553,744, Feb. 27, 1975, abandoned, which is a continuation of Ser. No. 378,186, Jul. 11, 1973, abandoned.

[51] Int. Cl.$^2$ .............................................. A61K 31/05
[52] U.S. Cl. ..................................................... 424/346
[58] Field of Search ......................................... 424/346

*Primary Examiner*—Stanley J. Friedman
*Attorney, Agent, or Firm*—Cushman, Darby & Cushman

[57] ABSTRACT

2,4-Dimethylphenol, and other dialkylphenols, administered in the picogram and femtogram range are used to present and/ameliorate the effects of DNA or RNA viruses such as herpes virus, measles virus, influenza virus and San Carlos virus.

4 Claims, No Drawings

METHOD OF USING DIALKYLPHENOLS AN ANTIVIRAL AGENTS

CROSS-REFERENCE TO RELATED APPLICATIONS

This application is a continuation-in-part of my earlier application Ser. No. 697,530 filed June 18, 1976, now abandoned, which in turn is a continuation of my earlier application Ser. No. 553,744 filed Feb. 27, 1975, now abandoned, which in turn is a continuation of my earlier application Ser. No. 378,186 filed July 11, 1973, now abandoned.

DESCRIPTION OF THE INVENTION

The present invention relates to the use of substituted phenols in ameliorating the effects of and preventing viral infections. The invention is more particularly concerned with the new application of compounds of the general formula:

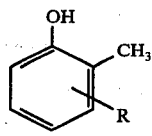

Formula I where R is lower alkyl, to systems containing either RNA or DNA viruses or mixtures thereof when used in concentrations in the picogram to femtogram range.

I have now found that compounds of formula I, above, and the pharmacologically acceptable salts thereof, when administered at levels in the picogram to femtogram range to a system comprising viral cells, exhibit anti-viral activity. Both RNA and DNA type viruses are affected by appropriate dosage levels of the compounds of formula I.

As the compounds of formula I there may be mentioned lower alkyl groups having from 1 to 5 carbon atoms, preferably R is methyl, such as 2,3-dimethylphenol, 2,4-dimethylphenol, 2,5-dimethylphenol, and 2,6-dimethylphenol; the preferred phenol is 2,4-dimethylphenol. These phenol derivatives have been described many times in the literature as compounds known per se and their methods of preparation are well known in the art. Further, many of these compounds are readily available in commerce. However, as far as the present inventor is aware, the use of these compounds by themselves or as the essential active ingredient in combination with a pharmaceutical carrier or diluent, have never been heretofore described as having anti-viral activity.

As an alternate source of certain compounds embraced in Formula I, the products described in my earlier patents U.S. Pat. Nos. 2,989,441 issued June 20, 1961 and 3,421,981, issued Jan. 14, 1969 may be used. The compounds of the present invention are isolated from the aforesaid products as follows: As mentioned in Example 1 of my earlier U.S. Pat. No. 2,989,441, the disclosure of which is hereby incorporated by reference, from the mother liquors remaining after crystallization of the cycloheximide, the residual amyl acetate is removed under vacuum the fraction boiling between 60° and 250° C. at about 200 microns was collected. This fraction was again distilled under vacuum, the portion boiling between 95° and 130° C being collected yielding 2,4-dimethylphenol. Crystals forming in the tubes leading to the condenser and that portion of the liquor containing 2,4-dimethylcyclohexane are discarded.

The present invention is based on my discovery that these compounds are effective in ameliorating the effects of and preventing viral growths and infections. Although generally effective against both RNA and DNA viruses, the compounds of Formula I are particularly effective against such viruses as San Carlos Virus (a DNA virus) and influenza virus (an RNA virus) in embryonated eggs, and other like viruses as more fully discussed and described below.

The compounds of Formula I above are used either in the form of the free base or, depending upon the dosage form provided, in the form of pharmacologically and pharmaceutically acceptable alkali addition salts, such as the alkali earth elements, for instance sodium, potassium, lithium or the like.

The anti-viral compositions of the present invention can be administered orally, parenterally, or intra-nasally and preferably as oral solid composition such as capsules, tablets and pills which contain the appropriate amount of the compound of Formula I and/or a pharmaceutically acceptable salt thereof per dosage unit. The solid compositions for oral administration can contain from about 1 femtogram to 10 miligrams and preferably from 100 picograms to 100 nanograms of the compound of Formula I per dosage unit. The liquid preparations for oral use are also prepared in such a manner that each dosage unit, such as one teaspoon or a given number of milliliters, contains from about 1 femtogram to 10 milligrams of active ingredient. When used in aqueous solution or in the presence of an organic solvent, such as lower alkanols, acetone, and the like, at a selected concentration, upon exposure to the atmosphere, the compounds of Formula I exert their own vapor pressure. As an illustration, a small quantity of the compound contained in a volatile organic solvent is placed on a cotton ball which is then put in close proximity to the subject animal. This procedure may be used as a convenient method of administration. Dosages in the femtogram to picogram range are also effective.

As used herein the term pharmaceutical carrier or pharmaceutical diluent denotes a solid or liquid which by itself is devoid of significant anti-viral activity and may be composed of a single substance or any number of substances such as solids, liquids or both. Some examples of the substances which can serve as pharmaceutical carriers in the compositions of the invention are gelatin capsules; sugars, such as lactose and sucrose; starches, such as corn starch and potato starch; cellulose derivatives, such as sodium carboxymethyl cellulose, ethyl cellulose, methyl cellulose, cellulose acetate phthalate; gelatin; talc; stearic acid; magnesium stearate; vegetable oils; such as peanut oil, cottonseed oil, sesame oil, olive oil, corn oil and oil of theobroma; propylene glycol; glycerin; sorbitol; polyethylene glycol; water, agar; alginic acid; isotomic saline; and phosphate buffer solutions, as well as other non-toxic compatible substances used in pharmaceutical formulations, coloring, flavoring and preservative agents may also be included.

Another aspect of my invention includes the treatment of laboratory animals, especially rats with a preferred compound of my invention 2,4-dimethylphenol (2,4 DMP) in the treatment of chronic respiratory disease (CRD). This disease is particularly troublesome to the commercial supplies of laboratory animals often destroying entire colonies of susceptable rats. In this procedure, the 2,4 DNP is conveniently administered in the drinking water of the animals.

EXAMPLES 1-15

The anti-viral activity of 2,4-dimethylphenol was studied in the following manner. Tissue cultures derived from human embryonic lung (HEL) were grown and maintained as monolayers in 32 ounce prescription bottles using growth medium consisting of 85% synthetic mixture No. 199 plus 15% unfiltered fetal bovine serum (FBS) adjusted to pH 7.4. Tube cultures of HEL cells were prepared in similar fashion and used in assays for anti-viral activity. During chemotherapy tests, the maintenance medium consisted of synthetic mixture No. 199 with 7.5% FBS. The virus spectrum in tissue culture consisted of two DNA viruses, a San Carlos virus isolated by Davis [see Science 133, 2059, 1961] and later identified as an adenovirus, and the HF strain of herpes simplex virus. In addition, a RNA virus represented by measles was included in the examples.

In performing the initial assays, the tissue cultures were treated prophylactically and the virus was treated in vitro with decreasing 2,4-dimethylphenol concentrations ranging from 200 ug ($2 \times 10^{-6}$) to 2 attograms (ag) ($2 \times 10^{-18}$) per ml. The procedure consisted of pretreating tube cultures of HEL cells for two to three days with growth medium containing varying concentrations of 2,4-dimethylphenol. After the prophylactic treatment, the test fluids were removed and replaced with fresh maintenance medium. At this time, 200 $TCID_{50}$ doses of virus were mixed in vitro with the same decreasing concentrations of the distillate used to pretreat the cells, then the mixture was inoculated into replicate culture of HEL cells so that the final incolum consisted of 100 $TCID_{50}$ doses of virus in tubes with 2,4-dimethylphenol at the same level used to prophylactically treat the cells.

The same number of infected control tubes were handled in the same way except that 2,4-dimethylphenol was omitted from all media. Culture tubes were rotated at 37° C. and examined daily for a period of 7 days for cytopathic activity (CPE). Results of such a screening test with San Carlos, herpes, and measles viruses treated with decreasing concentrations of 2,4-dinitrophenol is given in Table I. By this screening procedure, there was a slight but consistent inhibition of CPE produced by San Carlos virus in cultures with picograms of 2,4-dimethylphenol ($10^{-10}$ to $10^{-12}$ per ml of medium). At concentrations greater than the ug/ml level, or less than the picogram per ml range, the CPE San Carlos virus was similar to the untreated virus control. By the same token, the CPE of herpes virus was inhibited by both the $10^{-12}$ and $10^{-15}$ level, possibly indicating two active components. Measles CPE appeared to be inhibited at concentrations less than the $10^{-14}$ level of the tested compound. The results of these tests are reflected in Table I.

TABLE I

| | ANTIVIRAL ACTIVITY OF 2,4-dimethylphenol | | | |
|---|---|---|---|---|
| Example No. | Concentration in grams 2X | CPE* with 100 $TCID_{50}$** Doses of Virus | | |
| | | San Carlos | Herpes | Measles |
| 1 | $10^{-4}$ | 4+ | — | — |
| 2 | $10^{-5}$ | 2+ | — | — |
| 3 | $10^{-6}$ | 2+ | 3+ | 3+ |
| 4 | $10^{-7}$ | 1+ | 3+ | 3+ |
| 5 | $10^{-8}$ | 1+ | 2+ | 3+ |
| 6 | $10^{-9}$ | 1+ | 2+ | 2+ |
| 7 | $10^{-10}$ | 1+ | 2+ | 2+ |

TABLE I-continued

| | ANTIVIRAL ACTIVITY OF 2,4-dimethylphenol | | | |
|---|---|---|---|---|
| Example No. | Concentration in grams 2X | CPE* with 100 $TCID_{50}$** Doses of Virus | | |
| | | San Carlos | Herpes | Measles |
| 8 | $10^{-11}$ | 1+ | 2+ | 2+ |
| 9 | $10^{-12}$ | 2+ | 1+ | 2+ |
| 10 | $10^{-13}$ | 2+ | 2+ | 2+ |
| 11 | $10^{-14}$ | 3+ | 3+ | 1+ |
| 12 | $10^{-15}$ | — | 1+ | 1+ |
| 13 | $10^{-16}$ | — | 4+ | ± |
| 14 | $10^{-17}$ | — | 4+ | 1+ |
| 15 | $10^{-18}$ | — | 2+ | 0 |
| — | None (virus control) | 3+ | 3+ | 3+ |

*Cytopathic activity
**Tissue Culture Infected Doses (50%)
4+ = 100% of cells infected with selected virus
3+ = 75% of cells infected with selected virus
2+ = 50% of cells infected with selected virus
1+ = 25% of cells infected with selected virus
± = less than 10% infected
0 = no cells infected

EXAMINERS 16-25

The anti-viral activity of 2,4-dimethylphenol was evaluated in ovo against the PR-8 strain of influenza virus (RNA virus). Groups of 10-day embronated eggs were inoculated into the allantoic cavity with a mixture containing 10 $TCID_{50}$ doses of virus with various decreasing doses of 2,4-dimethylphenol ranging from 50 ng/egg to 1.6 pg/egg along with untreated virus controls. The eggs were incubated at 37° C. for 48 hours, candled, placed at 4° C overnight, then allantoic fluids harvested and tested individually for infectivity by hemagglutination. Also, allantoic fluids were pooled from each group of four eggs for each dose level and the average hemagglutinin titer determined using human type O red blood cells.

Table II shows that 2,4-dimethylphenol completely inhibited development of hemagglutinins in the allantoic fluid when given at 1.6 pg/egg. However, there was no inhibition at higher concentrations. The apparent anti-viral effect in eggs at only the picogram level is in keeping with the preceding examples agrees with and parallels the type activity observed in tissue cultures with the other viruses, namely maximum inhibiting activity at only picogram levels.

TABLE II

| In Ovo Activity of 2,4-dimethylphenol vs. Influenza PR-8 Virus | | | |
|---|---|---|---|
| Example No. | 10 $TCID_{50}$ Doses Virus plus 2,4-dimethylphenol Dose/Embryo | Hemagglutination at 48 hours | |
| | | %Eggs Positive | Pooled Avg. Titer 1: |
| 16 | 50 ng | 100 | 640 |
| 17 | 16 ng | 75 | 160 |
| 18 | 5 ng | 50 | 320 |
| 19 | 1.6 ng | 75 | 320 |
| 20 | 500 pg | 75 | 640 |
| 21 | 160 pg | 50 | 320 |
| 22 | 50 pg | 50 | 640 |
| 23 | 16 pg | 25 | 160 |
| 24 | 5 pg | 75 | 320 |
| 25 | 1.6 pg | 0 | 0 |
| — | None (virus control) | 75 | 640 |

EXAMPLES 26-35

Various phenols of Formula I were individually measured at concentrations ranging from $10^{-6}$ to $10^{-15}$ grams against San Carlos virus in the manner previously described, as compared with the cytopathic activity (CPE) according to the procedure of Examples 1-15 of 3,4-dimethylphenol which is not embraced by Formula I. According to the experiments the various 2-substituted phenols were studied by adding decreasing concentrations (log dilutions) of the compound beginning at one ug/ml of medium down to one fg/ml. The cells were treated with the appropriate phenol prophylactically and again therapeutically. One hundred tissue culture infective dose 50% ($TCID_{50}$) doses of the San Carlos virus were added to these cells, the tubes were rotated at 37° and examined daily for CPE. The results are reflected in Table III indicating that the 2,3,-, 2,4-, 2,5- and 2,6- derivatives, at various concentrations, exhibit anti-viral activity.

TABLE III

Results of study of Certain Dimethylphenols against San Carlos Virus in Tissue Culture (Human Embryonic Lung)

| Ex. No. | Conc. in grams 2X | CPE with $TCID_{50}$ Doses of Virus on the Dimethylphenols | | | | |
|---|---|---|---|---|---|---|
| | | 2,3- | 2,4- | 2,5- | 2,6- | 3,4- |
| 26 | $10^{-6}$ | 3+ | 3+ | 3+ | 2+ | 2+ |
| 27 | $10^{-7}$ | 2+ | 2+ | 2+ | 2+ | 1+ |
| 28 | $10^{-8}$ | 2+ | ± | 1+ | 1+ | 1+ |
| 29 | $10^{-9}$ | 1+ | ± | ± | 2+ | 1+ |
| 30 | $10^{-10}$ | 1+ | ± | 1+ | 1+ | 2+ |
| 31 | $10^{-11}$ | 1+ | 1+ | 1+ | 3+ | 2+ |
| 32 | $10^{-12}$ | 2+ | 1+ | ± | 2+ | 1+ |
| 33 | $10^{-13}$ | 1+ | 1+ | ± | 2+ | 2+ |
| 34 | $10^{-14}$ | 2+ | 2+ | ± | 1+ | 2+ |
| 35 | $10^{-15}$ | 2+ | 2+ | 2+ | 1+ | 1+ |
| | Virus Control | 3+ | 2+ | 2+ | 3+ | 2+ |

(See legend, Table 1)

EXAMPLE 36

Treatment of Chronic Respiratory Disease (CRD) in laboratory rats: chronic respiratory disease symptoms include coughing and wheezing accompanied by nasal secretions.

One-half of a colony of spontaneously hypertensive (SH) rats was treated with 2,4-dimethylphenol in their drinking water at a concentration of one part per billion. The other half of this colony was given only tap water, and both groups observed for 76 days. The second experiment was with a highly inbred strain (GM) of rats that were about to expire, because of chronic respiratory infection. These rats were observed for 150 days. Both groups, the SH rats and the GM rats, were not breeding because of their infections and were in seriously poor health.

They were only 42 SH rats left in the colony. They were divided into two groups of 21 rats each. Approximately one-half the sick rats were selected for each group. A certain number of these rats were very ill and others showed definite signs of respiratory problems. This was best observed as a brown secretion from the nose and wiped around the neck by the rat's front paws. The experimental group was treated continuously with one part per billion (1 PPB) of 2,4-dimethylphenol in their drinking fluid. Certain of these rats were so ill that they were near death when the experiment was started and they died in spite of treatment. The results of these experiments are given in the following table:

TABLE IV

Days post treatment with 1 PPB of 2,4-Dimethylphenol in their drinking water (distilled)

| | 0 | 14 | 22 | 29 | 36 | 43 | 76 |
|---|---|---|---|---|---|---|---|
| Total number of rats | 21 | 21 | 20 | 19 | 17 | 17 | 17 |
| Well animals | not eval. | 12 | 12 | 13 | 12 | 12 | 12 |
| Ill animals | not eval. | 8 | 7 | 4 | 5 | 5 | 5* |
| Dead animals | — | 1 | 1 | 2 | — | — | — |
| Controls - (tap water only) | | | | | | | |
| Total number of rats | 21 | 16 | 16 | 16 | 13 | 12 | 11 |

TABLE IV-continued

Days post treatment with 1 PPB of 2,4-Dimethylphenol in their drinking water (distilled)

| | 0 | 14 | 22 | 29 | 36 | 43 | 76 |
|---|---|---|---|---|---|---|---|
| Well animals | not eval. | 5 | 4 | 4 | 5 | 5 | 4 |
| Ill animals | not eval. | 11 | 12 | 9 | 7 | 6 | 3 |
| Dead animals | — | 5 | — | 3 | 1 | 1 | 4 |

*These five rats had minimal infection from visual observation, but were sacrificed along with the 3 ill rats in the Control Group.

At the end of 76 days of observation, there were 17 rats alive in the treated group; of these, 5 animals showed a trace of secretions around their necks, in spite of this, these rats were sacrificed to insure that a healthy colony remained. The control rats had only 7 survivors after 76 days of observation and there were only 4 rats that were apparently healthy out of the 21 animals starting the experiment; the other three rats were so ill in this group that if the experiment had continued they would have died. The four healthy animals in this group were combined with the treated group and then all continued on the treatment with 2,4-dimethylphenol (1 PPB) in their drinking fluid; more than 2 years elapsed. These animals began to breed, and the colony is now healthy.

EXAMPLE 37

The second experiment was run concurrently with Example 36, but this time the animals were the highly inbred GM strain. A number of these animals were ill with chronic respiratory disease and unable to breed. These rats were randomly divided into two groups of 26 each. The experimental group received 1 PPB of the 2,4-dimethylphenol in their drinking water and the control group received only tap water. Both groups were evaluated at intervals as reported in the following table:

TABLE V

Days post treatment with 1 PPB of 2,4-Dimethylphenol in their drinking water (distilled)

| | 0 | 58 | 66 | 73 | 80 | 150 |
|---|---|---|---|---|---|---|
| Total number of rats | 26 | 26 | 26 | 26 | 25 | 56* |
| Well animals | not eval. | 23 | 23 | 24 | 25 | 53 |
| Ill animals | not eval. | 3 | 3 | 2 | 0 | 3** |
| Dead animals | — | — | — | — | 1 | — |
| Controls (tape water only) | | | | | | |
| Total number of rats | 26 | 26 | 24 | 24 | 24 | 24 |
| Well animals | not eval. | 15 | 18 | 18 | 16 | 16 |
| Ill animals | not eval. | 9 | 6 | 6 | 8 | 8 |
| Dead animals | — | 2 | — | — | — | — |

*The experimental group began to breed and there were 31 new born rats and all appeared healthy. The control group did not start breeding up to the 150th day of observation.
**The three rats listed as ill had only a trace of secretion on their necks, while the 8 animals in the control group were obviously ill and were sacrificed at the end of the observation period.

Experimental rats for hypertensive study were later required so all of the ill GM rats remaining were sacrificed and experimental and control groups were combined. All these animals continued to receive 1 PPB of 2,4-dimethylphenol in their drinking fluid. The total time now was over 2.5 years and the colony has continued to thrive. The total number of rats now number about 400 and this does not include those animals used for experimental studies in hypertension for the past 2½ years.

EXAMPLE 38

Most researchers disagree on the etiology of chronic respiratory disease in rats. Some say that it is of viral origin others think that it is caused by mycoplasma pulmonis. It appears that either a virus or Mycoplasma can cause the syndrome in the rat.

Attempts were made to test the effect of infecting rats with Mycoplasma pulmonis (ATCC 19612) so that they could transmit the disease to their cage mates and, also allowed them to breed. This was also done to test if the mothers would pass the infection on to their litters. These rats were purchased from a laboratory in Indianapolis, Indiana and they were divided into 6 groups with male animals in each group. In the 5 experimental groups, a total of 15 female rats out of 30, and in the control group 4 female rats out of 8 were infected intranasally with Mycoplasma pulmonis (ATCC 19612). There were two male rats per experimental group and 3 for the controls totaling 13 male rats, and none of these were infected with M. pulmonis.

The experimental groups (8 rats each) and control group were treated as follows:

| Group 1 | 1 PPM | 2,4 DMP |
|---|---|---|
| Group 2 | 100 PPB | 2,4 DMP |
| Group 3 | 10 PPB | 2,4 DMP |
| Group 4 | 1 PPB | 2,4 DMP |
| Group 5 | 100 PPT | 2,4 DMP |
| Group 6 | control | (distilled) |

All rats were fed ad libitum rat chow, and their cages were cleaned 5-6 times weekly. For the 5 experimental groups, the 2,4 DMP was dissolved in distilled water used for their drinking fluid while the control only received distilled water. There were times when the rats spilled excessive amounts of their drinking water and this caused a certain amount of the phenol to be evaporated from these cages, particularly those groups receiving the higher concentrations of the phenol. This way, it was possible for the controls to inhale a small but indefinite amount of the phenol which is volatile. All animals were kept in the same laboratory room.

All the male animals (13) were sacrificed after 14 days, and after impregnating the females. Their blood was collected by heart puncture, and the animals lungs were saved in 10% formalin for pathology. All the female rats (18) that were not infected, except one, intranasally with M. pulmonis were sacrificed 30 days post infection of their cage mates. All the young born to these rats (non-infected), during this time were also sacrificed. The blood and lungs from the adult females were saved for study.

The 19 female rats infected with M. pulmonis and one non-infected female were allowed to raise their litters so that the young could be weaned, and then they were sacrificed 58 days post infection, saving their blood and lungs for study. The only group that did not have any offsprings was the ones receiving 100 parts per trillion of the phenol in their drinking water.

When the offsprings from the M. pulmonis infected mothers were 40-50 days old a proportionate number selected at random were sacrificed, saving blood and lungs for study:

Treatment of 40-50 days old rats and the number sacrificed per group
  Group 1 — 1 PPM of 2,4 DMP — 4 out of 13
  Group 2 — 100 PPB of 2,4 DMP — 4 out of 11
  Group 3 — 10 PPB of 2,4 DMP — 7 out of 22
  Group 4 — 1 PPB of 2,4 DMP — 7 out of 20
  Group 5 — 100 PPT of 2,4 DMP — 0 out of 0
  Group 6 — Controls, distilled water — 10 out of 30

Two weeks later one-fourth of the remaining offsprings were sacrificed for study and the other three-fourths of these young rats were separated.

The pathology of the lungs was inconclusive because the group of animals purchased for this study already had lung involvement. The three female rats were sacrificed that had been infected intranasally with Mycoplasma pulmonis and treated for 58 days with one part per billion of 2,4-dimethylphenol in their drinking water. Their lungs were, for all practical purposes, clear of infection when compared with the other four groups and the controls. The lungs of the other 48 rats starting this experiment showed significant pathology to warrant a study to determine the cause of the infection.

The serum of each rat sacrificed was tested for antibodies for Mycoplasma. The results showed that only two out of the 19 rats infected intranasally with the Mycoplasma had detectable titers. One of these rats was in the group receiving one part per million of the phenol and other was a control. Therefore, it was concluded that the Mycoplasma pulmonis was not the cause of the lung infection in these rats, but there was still enough pathology evident in these lungs to suspect some unknown infection. Consequently, the serum of the control rat showing a low titer for Mycoplasma pulmonis was screened by a commercial laboratory for virus infections commonly associated with rats. Their report showed only pneumonia virus of mice (PVM) as the infective agent. This series of experiments was somewhat inconclusive as to whether or not the Mycoplasma pulmonis had failed to infect the rats or if 2,4 DMP had substantially prevented the infection.

All blood serums saved from these experiments were tested for PVM titers. Sera from eight of the 13 males sacrificed at 14 days had detectable titers. All three of these controls had titers indicating PVM infection leaving 5 treated rats with titers for PVM. In the 18 non-infected female rats that were sacrificed after 30 days two rats were negative for PVM titers, one was in the 1 PPM and the other was in the 1 PPB treated groups. All controls showed positive titers. The sera of the 19 rats infected with the Mycoplasma, two in the one part per million and two in the 100 parts per billion failed to show titers for PVM. The group (3 rats) receiving one part per billion showed a titer of 1:10 for PVM which is the lowest detectable titer.

These 51 rats purchased for this experiment evidently contacted the PVM before the start of the experiment and the 2,4-dimethylphenol appeared to have had an effect on this virus so as to depress its passage to other animals. It is well known that animals will exhibit antibody titers for a virus after recovery from an infection. This is the basis of any immunization program to control such viral diseases as influenza, measles, etc. The striking part of this experiment was that not one of the entire group of offsprings (47) tested had detectable titers for PVM. The only group that should have shown titers was the controls. This can be readily explained because the controls were housed in the same room with the treated groups and these treated rats spilled considerable amounts of their water each day, thus making 2,4-DMP vapors available for the control group to inhale.

Based upon the above experiments, the concentration recommended is one part per billion in the drinking fluid. Since an adult rat drinks approximately 30 ml per day, then the animal received 30 nanograms of 2,4-dimethylphenol per day or about 100 nanograms per kg per day. This dose level corresponds well to the most effective concentration found for tissue culture tests when testing for antiviral activity as reported in the preceding examples.

I claim:

1. A method of inhibiting the growth of a virus selected from the group consisting of San Carlos virus, herpes virus, measles virus, and influenza virus in cells infected with said virus, consisting essentially of administering to said cells from 1 femtogram to 100 nanogram of 2,4-dimethyl phenol or the pharmaceutically acceptable addition salts thereof.

2. The method of claim 1 wherein from 100 picograms to 100 nanograms of 2,4-dimethylphenol is administered.

3. A method of inhibiting the growth of a virus-related chronic respiratory disease in an animal suffering therefrom, consisting essentially of administering to said animal from 1 femtogram to 100 nanogram of 2,4-dimethylphenol or a pharmaceutically acceptable addition salt thereof.

4. The method of claim 3 wherein from 50 to 200 nanograms per kilogram per day of 2,4-dimethylphenol is administered.

* * * * *